(12) United States Patent
Lefebvre Du Grosriez (10) Patent No.: US 6,475,346 B2
(45) Date of Patent: Nov. 5, 2002

(54) APPARATUS TO CLAMP AT LEAST ONE NON-WOVEN OR PAPER SHEET, METHODS IMPLEMENTING SUCH APPARATUS, AND ARTICLE MADE BY SUCH METHODS

(75) Inventor: Carol Lefebvre Du Grosriez, Oberhergheim (FR)

(73) Assignee: Georgia-Pacific France, Kunheim (FR)

( * ) Notice: Subject to any disclaimer, the term of this patent is extended or adjusted under 35 U.S.C. 154(b) by 0 days.

(21) Appl. No.: 09/839,406

(22) Filed: Apr. 23, 2001

(65) Prior Publication Data

US 2002/0060032 A1 May 23, 2002

(30) Foreign Application Priority Data

Apr. 28, 2000 (EP) .............................................. 00401191

(51) Int. Cl.⁷ .............................. B31B 1/00; B31B 5/00
(52) U.S. Cl. ........................ 162/362; 162/109; 156/209
(58) Field of Search ................................ 162/109, 110, 162/114, 116, 117, 204, 205, 305, 358.1, 361, 362, 416; 101/3.1, 5, 6, 7, 22, 23, 32; 156/163, 209, 164, 228, 183, 543, 199, 544; 29/895.32; 264/280, 284, 286; 492/17, 18, 20, 24, 25, 30; 493/345–347, 380–382; 425/500

(56) References Cited

U.S. PATENT DOCUMENTS

| | | | | |
|---|---|---|---|---|
| 3,893,795 A | * | 7/1975 | Nauta ........................... | 425/403 |
| 4,803,032 A | * | 2/1989 | Schulz ......................... | 264/284 |
| 5,096,527 A | * | 3/1992 | Biagiotti ...................... | 156/209 |
| 6,032,712 A | * | 3/2000 | Biagiotti ...................... | 156/358 |
| 6,170,393 B1 | * | 1/2001 | Hook et al. .................... | 101/6 |
| 6,251,207 B1 | * | 6/2001 | Schultz et al. ............... | 156/209 |

* cited by examiner

Primary Examiner—Peter Chin
Assistant Examiner—Eric Hug
(74) Attorney, Agent, or Firm—Breiner & Breiner, L.L.C.

(57) ABSTRACT

The invention relates to apparatus clamping at least one paper or non-woven sheet and including two cylinders which run substantially tangent to one another. At least one of the cylinders has on its surface and in a zone that makes contact with the sheet a clamping band having first salient elements. The interaction of the two cylinders in the presence or absence of the sheet subtends an active surface during the rotation of the cylinders. In the invention, at least one of the cylinders has on its surface and in a zone (nip) that makes contact with the other cylinder by means or not of the sheet a load compensating band having second salient elements. This band is selected so that the variation of the consecutive instantaneous active surfaces of the clamping band and of the load compensating band is less than the variation of the consecutive instantaneous active surfaces of the clamping band alone. The invention applies in particular to converting paper or non-woven sheets in the manufacture of absorbent paper items, such as tissues or table napkins.

32 Claims, 6 Drawing Sheets

APPARATUS TO CLAMP AT LEAST ONE NON-WOVEN OR PAPER SHEET, METHODS IMPLEMENTING SUCH APPARATUS, AND ARTICLE MADE BY SUCH METHODS

FIELD OF INVENTION

The invention relates to apparatus for clamping at least one non-woven or paper sheet and use thereof in converting the sheet into finished products once the sheet has been manufactured by a wet or dry process.

BRIEF DESCRIPTION OF THE INVENTION

More specifically, the invention relates to apparatus for clamping at least one non-woven or paper sheet and includes two substantially mutually tangent cylinders between which the sheet is made to run. In this apparatus, at least one of the cylinders, on its surface and in a zone that makes contact with the sheet, is fitted with a clamping band having first salient elements. The interaction between the two cylinders during their rotation in the presence or absence of a sheet subtends an active surface. This active surface is described in greater detail below.

Herein the term "paper" denotes any product based on paper fibers, for example tissue paper and absorbent paper products made by either a dry or wet process. As regards the latter, the paper fibers are bonded by a thermoplastic bonding agent, such as latex or heat-melting fibers. Some paper products also may be composed of cellulose fibers other than paper fibers and on occasion the paper products may include some synthetic or artificial fibers.

The invention also covers non-woven products.

The invention furthermore applies to making tissue paper goods and, in particular, paper napkins, handkerchiefs, paper towels, sanitary paper or the like.

In general, these goods are made from one or more superposed paper plies that are subjected to clamping. There can be several purposes for such clamping.

As shown further below, the clamping action applied to one or more plies between two preferably oppositely rotating cylinders of the apparatus, as a function of such operating conditions, in particular as pressure, and the kind of cylinders involved, can entail the following:

plain joining of the plies to each other, whether or not additives are used, depositing an additive on the surface of one ply, for example applying adhesive, ink, lotion or the like, marking one or more plies running through the apparatus.

The expression "plain joining" herein denotes that several plies are mutually attached by mere pressure, with or without adhesive. In case adhesive is used, the apparatus is fitted with an engraved cylinder and a mating cylinder which is the adhesive-bearing and depositing cylinder.

Herein the expression "marking" denotes any kind of deformation of the non-woven or paper sheet that might be implemented by running the sheet through two cylinders of which one at least is fitted with a clamping band. By clamping the paper sheet against the surface of a mating cylinder, the clamping band causes the sheet to be marked either by compressing the paper fibers ("marking" in the rigorous sense), or by deforming into salients (embossing) in patterns which correspond to salient elements configured on the clamping band.

Depending on apparatus application, the clamping band imparts a pattern, which is permanent or not, to the non-woven or paper. At the time the cylinders are in mutual contact by means of the inserted non-woven or paper sheet, any applied pressure will entail marking by the clamping band. The magnitude of this pressure (relatively weak if two plies are combined) may be such that this marking will be slight and impermanent. In such a case, generally no marking at all will be visible on the finished product. At high pressure, marking will be permanent and visible on the finished product.

The clamping band includes first salient elements engraved on its cylindrical surface. These elements can be configured in such a way that they constitute one or more, continuous or discontinuous salient zones around the cylinder. The elements can be geometrical or not. The elements can be discrete, for example dots or dashes, or the elements can be continuous or discontinuous lines, or otherwise. Patterns also can be subtended by an absence of salient elements or tips. For that purpose, tip-free zones in a desired pattern on the paper are present on a surface otherwise containing a regular array of tips.

Depending on what kind of mating cylinder is used and the pressure applied by the cylinders on the paper sheet, different kinds of markings can be implemented.

Accordingly, the cladding of the mating cylinder can be a relatively flexible material when compared with the cladding of the cylinder bearing the clamping band. Also, the mating cylinder can be made of any material which is similar to that of the clamping-band bearing cylinder. The external cylindrical surface of the mating cylinder can be smooth and also can be fitted with hollow elements complementary to the clamping band's salient elements. Moreover, the external cylindrical surface of the mating cylinder can be fitted with salient elements which are identical with those of the clamping band in such a way that the paper sheet is clamped at a given pressure between two mutually opposite salient elements.

Depending on these various parameters, the kind of marking used may entail different effects, in particular increasing the paper thickness (embossing), increasing the paper's absorption, interlinking the various plies resulting in forming the sheet of paper, an especially aesthetic marking but also a decrease in paper thickness (marking in the rigorous sense) in the pattern zones.

In all cases, the paper sheet is clamped between two cylinders of which the axes run substantially parallel and which are made to approach each other radially and which are driven into rotation once the sheet of paper runs between them.

Accordingly, the paper is clamped in the cylinders' contact zone.

In theory, this contact zone is a line running parallel to the axes of rotation of the two cylinders, but in practice the contact zone assumes a certain width depending on the cylinders' circumference (diameter) and width, the compression they exert, the features (thickness, hardness, etc.) of the cylinder claddings and the features (thickness) of the clamped non-woven or paper. As a result, the zone constitutes a contact strip running axially along a main contact generatrix. This zone is not necessarily regular width-wise. The zone can be rectangular, centrally concave or convex, etc. This pinching zone in the form of a contact strip between the two cylinders is generally called by the English word "nip".

Be it borne in mind that when the thickness of the non-woven or paper sheet is greater than the inter-cylinder gap, the nip also may be present between the cylinders and contact set up through the intermediary of the sheet.

With or without the sheet between them, the two cylinders interact during their rotations and subtend an active surface subtended by the salient elements arrayed on the cylinder surfaces. More specifically, the active surface of the clamping band includes the surface of the salient elements which by means of the sheet make contact with their mating part and, in some cases and in particular if the mating part is made of rubber, in contact with the surface of part of the zones situated between the salient elements, where the zones on account of the deformation of the mating part and of the paper also can make contact by means of the sheet of paper with the mating part. In the latter case, the applied pressure varies between the peaks of the salient elements and the contact zones between the salient elements.

An active surface which is termed the "instantaneous active surface" is associated with each nip.

Accordingly, the consecutive instantaneous active surfaces by means of which the two cylinders cooperate with one another vary as a function of the salient elements of the clamping band and, furthermore, as a function of the area of the contact zone (nip).

Figure 2:
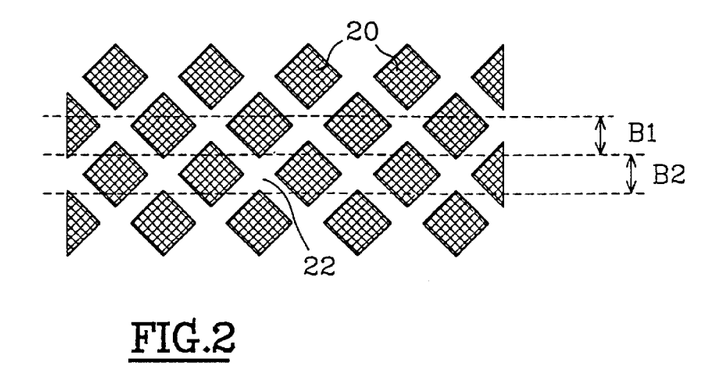
FIGS. 2 and 3 show two illustrative configurations of salient elements of a clamping band.
Figure 3:
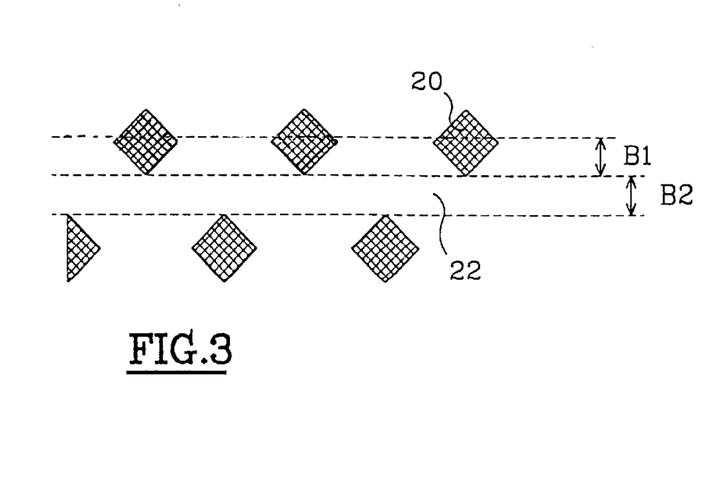

FIGS. 2 and 3 show two illustrative configurations of salient elements for a clamping band.

FIGS. 2 and 3 show two defined bands B1 and B2 representing the contact zones of two cylinders at two of their angular positions.

In the example of FIG. 2, and looking at the contact zones B1 and B2, the instantaneous active surface of the band B1 is identical with that of the band B2.

In the example of FIG. 3, the two bands B1 and B2 exhibit two much different consecutive instantaneous active surfaces because, unlike the case for the band B1, the surface of the salient elements of the band B2 is zero.

In case the cylinders exert compression work and as regards these cylinders' angular position corresponding to the band B2, interaction takes place between these two mutually contacting cylinders, but this interaction is much different from that of these same cylinders in the angular position corresponding to the band B1. Accordingly, in the configuration of the salient elements of FIG. 3, the stresses undergone by the cylinders vary substantially in time when these cylinders are rotating.

Such varying interaction stresses on the two cylinders which implement clamping substantially degrades the mechanical strength and service life of these cylinders and of any apparatus in general (vibrations). This problem arises in many apparatus which clamp a non-woven or paper sheet between two cylinders of which at least one is engraved.

Accordingly, it is an object of the invention to improve apparatus clamping a non-woven or paper sheet and offering longer service life of the cylinders and the overall equipment. Another object of the invention is to create widely varying patterns on the sheet by eliminating any constraints regarding the regularity of interaction between the cylinders due to the salient elements, whereby pattern selection would be reduced.

Accordingly, it is henceforth possible to select different shapes, distributions and density patterns.

For that purpose, the invention provides a non-woven or paper clamping apparatus of the above described kind which is characterized in that at least one of the cylinders is fitted at its surface and in a zone designed to be in contact with the other cylinder through an intermediary or not of the sheet with a load-compensating band including secondary salient elements, the band being selected in such a manner that the consecutive instantaneous active surface variation of the clamping band and of the load-compensating band is less than the variation of the consecutive instantaneous surfaces of the single clamping band.

Other features of the invention, whether considered singly or in combination, include the following features:

variation among the consecutive instantaneous active surfaces of the clamping band and the load compensating band is substantially zero, the width of the active surface corresponding to the single load compensation band varies along the circumference of the cylinder on which this band was created as a function of the instantaneous active surface of the single clamping band, the two cylinders rotate in mutually opposite directions, the first salient elements of the clamping band are identical with or different from the second salient elements of the load compensating band, the load compensating band is configured on one cylinder outside the clamping band, the second salient elements of the load compensating band are different from the first salient elements of the clamping band and the load compensating band at least partly straddles the clamping band, at least one of the cylinders bears at least one clamping band and at least one load compensating band, the height of the load compensating band's salient elements is substantially identical with the height of the clamping band's salient elements, the height of the load compensating band's salient elements is greater than the height of the clamping band's salient elements, the height of the load compensating band's salient elements is less than the height of the clamping band's salient elements, the load compensating band includes a rolling zone which determines a minimum width of the active surface of the load compensating band, the rolling zone of the load compensating band is radially configured at the same place as the remainder of the load compensating band, the rolling zone of the load compensating band is configured radially outward from the remainder of the load compensating band, the rolling zone of the load compensating band is configured radially inward relative to the remainder of the load compensating band, several load compensating bands are fitted on the same cylinder, each load compensating band includes one rolling zone.

Furthermore, the invention also relates to a cylinder clamping a non-woven or paper sheet, which is characterized in that it includes a load compensating band defined by one of the above features.

Also the invention relates to equipment including at least one apparatus defined by any of the above features.

Further, the invention relates to a method combining at least two non-woven or paper plies and characterized in that it includes the operation of apparatus having any of those features, wherein the sheets are clamped between the two cylinders near the clamping band in the presence or absence of adhesive.

The invention also relates to a marking procedure applied to at least one non-woven or paper sheet which is characterized in that it operates apparatus with the same features wherein the clamping band imparts a pattern to the non-woven or paper sheet by deforming this sheet clamped between the two cylinders.

The invention also relates to any procedure using the apparatus of the invention to apply additives to a non-woven or paper sheet.

The invention also relates to a procedure for manufacturing tissue paper articles which include at least two plies and is characterized in that the plies are mutually joined by marking, embossing or combining.

Lastly, the invention provides a non-woven or paper article including at least one ply and characterized in that it is marked using the above marking procedure.

Other features and advantages of the invention are elucidated in the comprehensive description below and in the attached drawings.

DETAILED DESCRIPTION OF PRESENTLY PREFERRED EMBODIMENTS

The invention is elucidated below in relation to a clamping apparatus as described in greater detail below. This apparatus implements the deformation of a sheet of paper, in this case its marking.

Figure 1:
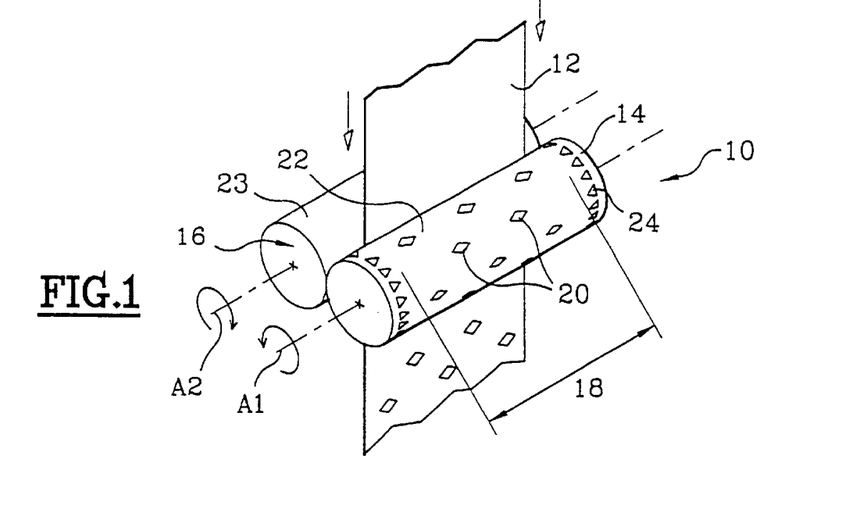
FIG. 1 is a schematic perspective of the active surfaces of apparatus clamping a paper sheet which moves between two cylinders.

FIG. 1 shows an apparatus 10 wherein a paper sheet 12 is marked by being made to run between two cylinders 14, 16 of which the axes A1 and A2 are mutually parallel and which rotate in a synchronized manner but in opposite directions about the axes.

The sheet of paper 12 can be replaced by two paper plies and in that event the object of their clamping is not only to mark them but also to affix them to each other. This marking (in this example in the form of embossing) also enables increasing the paper's absorption. In all instances the most aesthetic marking is desired.

In the example shown, the cylindrical surface 22 of one of the cylinders 14 is engraved so as to exhibit a clamping band 18 fitted with a plurality of salient elements 20.

In this embodiment, the second cylinder 16, called the mating cylinder, is fitted with a smooth surface 23.

The two cylinders 14 and 16 cooperate by means of a contact zone of their cylindrical surface 22, 23. This contact zone, also called "nip", is not restricted to a straight generatrix, and is shown here in the form of an axial band in the circumferential direction of the cylinders 14, 16, the direction also being the direction of advance of the paper sheet 12.

For each angular position of the cylinders 14, 16 corresponding to a particular position of the paper sheet in the direction of advance, the salient elements 20 of the clamping band 18 situated in the nip therefore make contact with the paper sheet 12 and clamp some of the sheet's portions against the cylindrical surface 23 of the mating cylinder 16.

The nip dimension in the circumferential direction varies in particular in relation to the materials constituting the cylinder 14, 16, their diameters and the gap between them.

As disclosed in this invention, the engraved cylinder 14 also is fitted on its cylindrical surface 22 with two load compensating bands 24, each configured in this embodiment at an axial end of the engraved cylinder on either side of the clamping band 18 outside the zone of the cylinder 14 which is opposite the sheet of paper 12.

Figure 4:
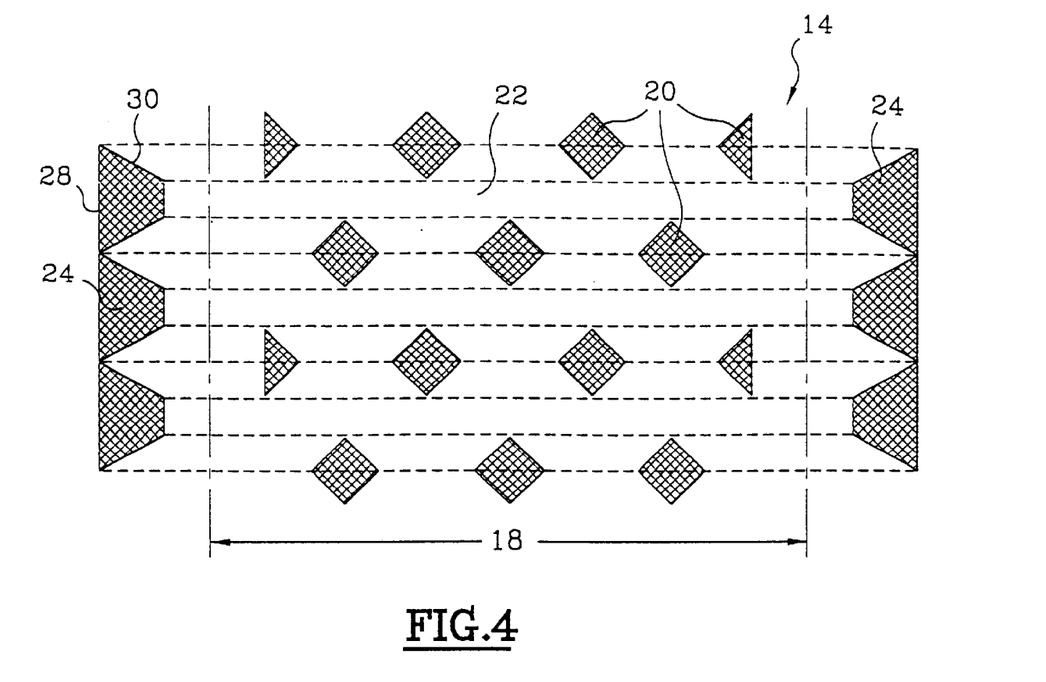
FIGS. 4, 5 and 6 schematically show the active surfaces of a clamping band and of at least one load compensating band which are fitted on a cylinder of an apparatus of the invention.
Figure 5:
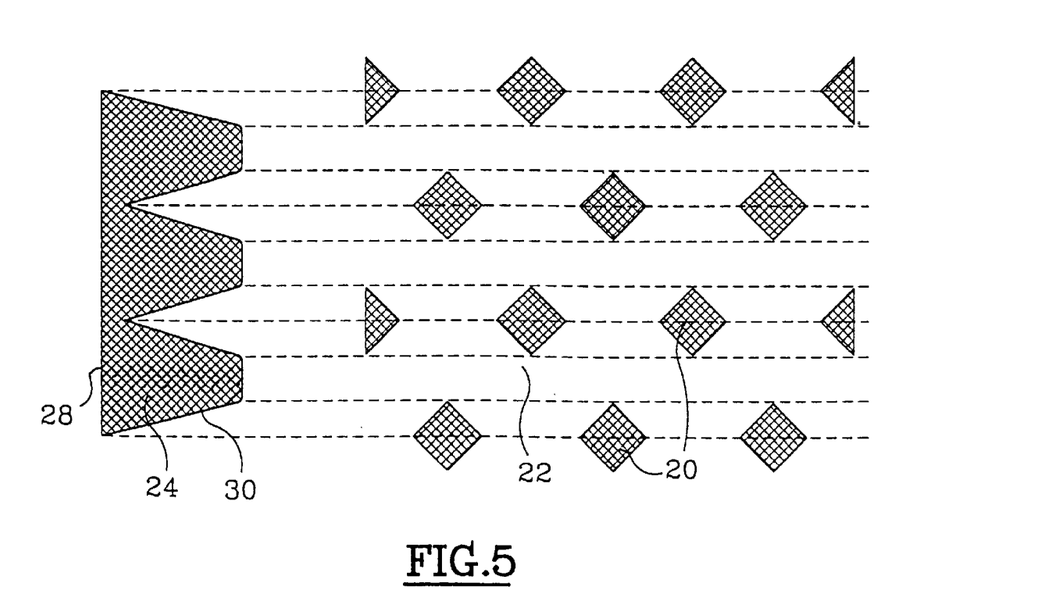
Figure 6:
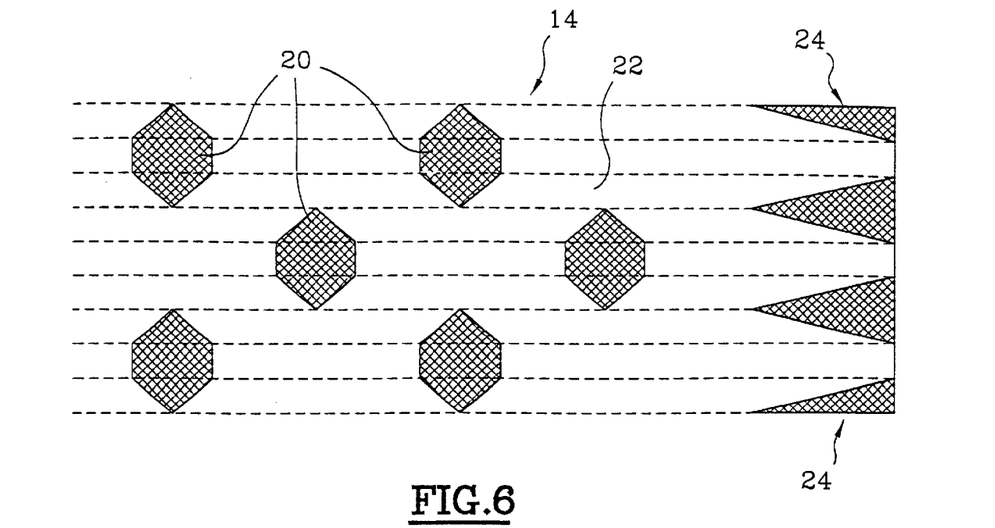

As regards FIGS. 4, 5 and 6, the active surfaces are solely those of the salient elements.

FIG. 4 is a geometrically developed (flattened) view of the salient elements of the surface of the cylinder 14.

In this embodiment, the salient elements 20 are diamond-shaped or triangular. These are simple geometric shapes. The invention of course can be carried out using more complex and ornamental patterns. Also, the salient elements 20 can be in the form of dots, thereby reducing the active surface of the clamping band 18 which is designed to make contact with the mating cylinder 16.

It must be borne in mind that with respect to the clamping band, some salient element configurations can be denser than others consisting of lines and hence can exhibit a larger active surface. A given configuration of lines transformed into dots allows reducing the surface of the active band that makes contact with the mating cylinder through the intermediary of the sheet of paper.

The expression "load compensating band" denotes a salient element zone compensating the stress changes due to the clamping band's active surface. This zone can be composed of independent salient elements (small, pin-type elements) configured in a discrete manner or it can be in the form of a continuous band.

As regards the embodiment of FIG. 4, a load compensating band 24 is configured on each side of the clamping band 18. However, as shown in FIG. 5, a single load compensating band 24 also can be used and be situated at one of the axial ends of the cylinder 14, in which case this band is wider.

Therefore, each load compensating band 24 is designed to come to rest against the cylindrical surface 23 of the mating cylinder 16 without mediation by the paper sheet 12 and as regards the embodiment of FIG. 1 and through the intermediary of the paper sheet 12 in other cases as is described farther below. At each angular position of the cylinders 14, 16, the instantaneous active surface of the load compensating band 24 is its part situated in the nip of the two cylinders.

As shown in FIGS. 4–6, the active surface of the load compensating band 24 varies. It varies inversely to the active surface of the clamping band 18 for the same nip.

In this embodiment, the variation of the consecutive instantaneous active surfaces of the clamping band 18 and to the load compensating band 24 is substantially zero over a full cylinder revolution.

As a result, the interactive stress of the two cylinders 14, 16 is substantially constant and the apparatus will wear well.

As regards the embodiments of the invention shown in FIGS. 4–6, the load compensating band 24 includes a first edge 28 which, when geometrically developed, is straight, and a second, non-rectilinear edge 30 of which the contour determines the width of the load compensating band 24. However, the load compensating band 24 also can be bounded by two non-rectilinear edges.

In order to define the shape of the load compensating band, the cylinder circumference is analyzed by consecutive measurement zones. These zones can assume a value corresponding to one nip. However, the thinner the zone, the more precise the load compensating band and the less significant load variations will be. Therefore, the measurement zone preferably is less than the nip.

As shown in FIG. 6, the width of the load compensating band 24 can be zero at some sites. This will be the case when, at a particular nip, the active surface of the clamping band 18 reaches a maximum value.

However, to improve the service life of the claddings of the cylinders 14, 16, interruption zones in the load compensating band 24 is preferably are averted. In the long run, local stress discontinuity in the load compensating band may harm the cylinder cladding.

Figure 7:
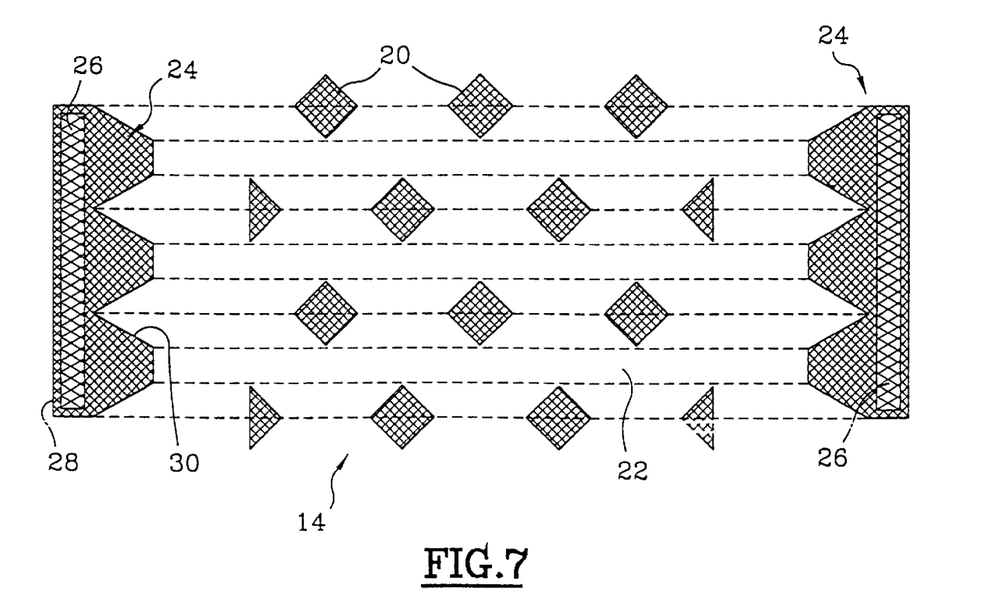
FIG. 7 is a view similar to FIGS. 4 through 6 wherein the apparatus' load compensating bands have a rolling zone.

As shown in FIG. 7, the load compensating band 24 also can be fitted with a constant width rolling zone 26 which in a way amounts to a minimum interaction surface for the two cylinders 14, 16.

This rolling zone 26 preferably is adjacent to the remainder of the load compensating band 24 and as a result runs continuously around the cylinder axis.

When the load compensating band 24 has two non-rectilinear edges, the rolling zone 26 illustratively is situated at the center of the band 24.

Figure 8:
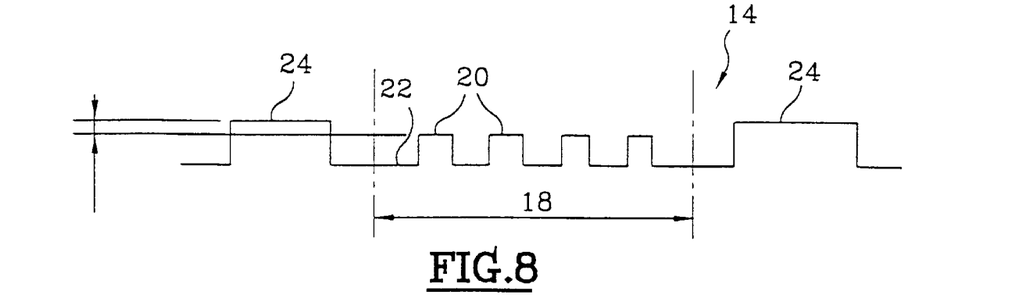
FIGS. 8–10 are plots schematically illustrating various positions of the salient elements of the clamping band relative to those of the load compensating band.
Figure 9:
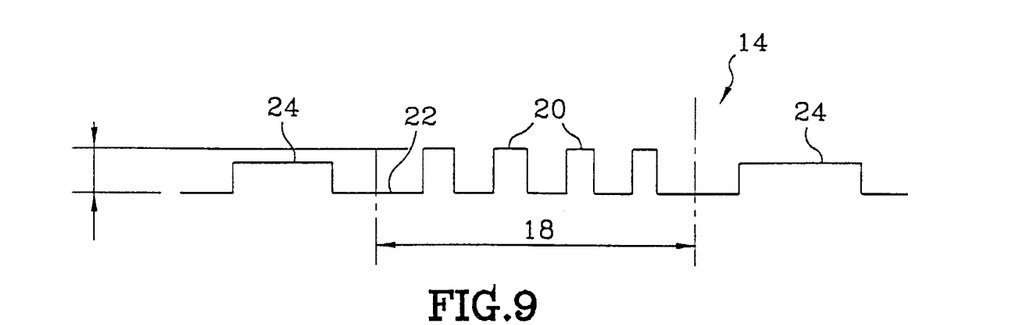
Figure 10:
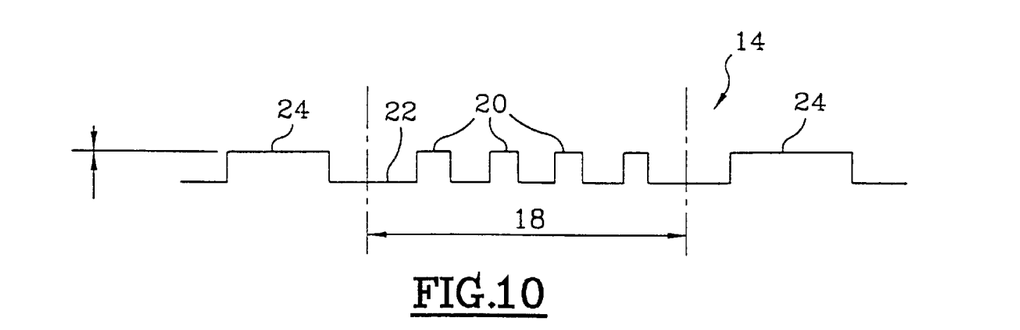

FIGS. 8 through 10 are three plots schematically indicating the position of the salient elements of the clamping band 18 relative to those of the load compensating band 24.

As regards the embodiment of FIG. 8, the height of the salient elements of the load compensating band 24 exceeds the height of the salient elements 20 of the clamping band 18. In FIG. 9, on the other hand, the height of the salient elements 20 of the load compensating band 24 is less than that of the salient elements 20 of the clamping band 18, whereas, in FIG. 10, the height of the salient elements of the load compensating band 24 is substantially the same as that of the salient elements of the clamping band 18.

Figure 11:
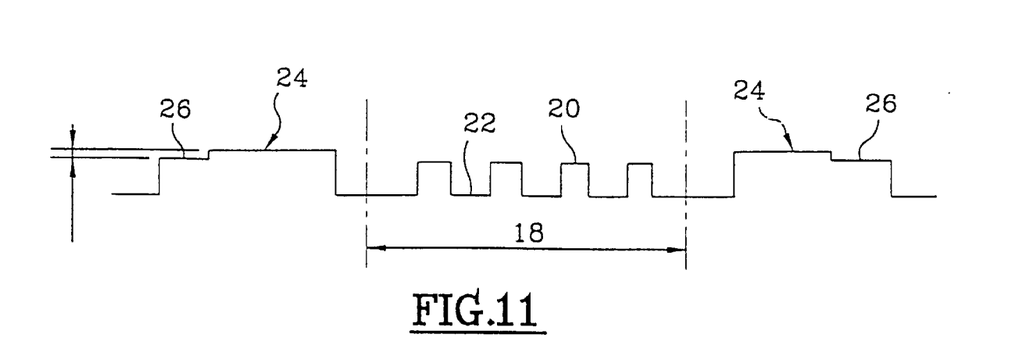
FIG. 11 is a plot similar to those of FIGS. 8–10 illustrating a practical relative position in the radial direction of the rolling zone of a load compensating band relative to latter.

FIG. 11 is a plot of the rolling zone 26 being configured radially more inward than the remainder of the load compensating band 24. However, the rolling zone 26 can be radially situated at the same place as, or more outwardly than, the remainder of the load compensating band 24.

As regards the embodiments of FIGS. 4 through 11, both the load compensating band 24 and the clamping band 18 rest on the same cylinder 14. This feature is especially advantageous when the second cylinder 16 is smooth because only one of the two cylinders can be engraved in order that the invention does not entail significant further cost. In principle, however, each band 18 and 24 can rest on one of the cylinders 14, 16. In the event the load compensating band is not located on the cylinder fitted with the clamping band's salient elements, adequate angular regulation must be provided between the two cylinders in order that the load compensation band be in register with the distribution of the clamping band's salient elements. Again, the rolling zone can be fitted onto the second cylinder 16.

Figure 12:
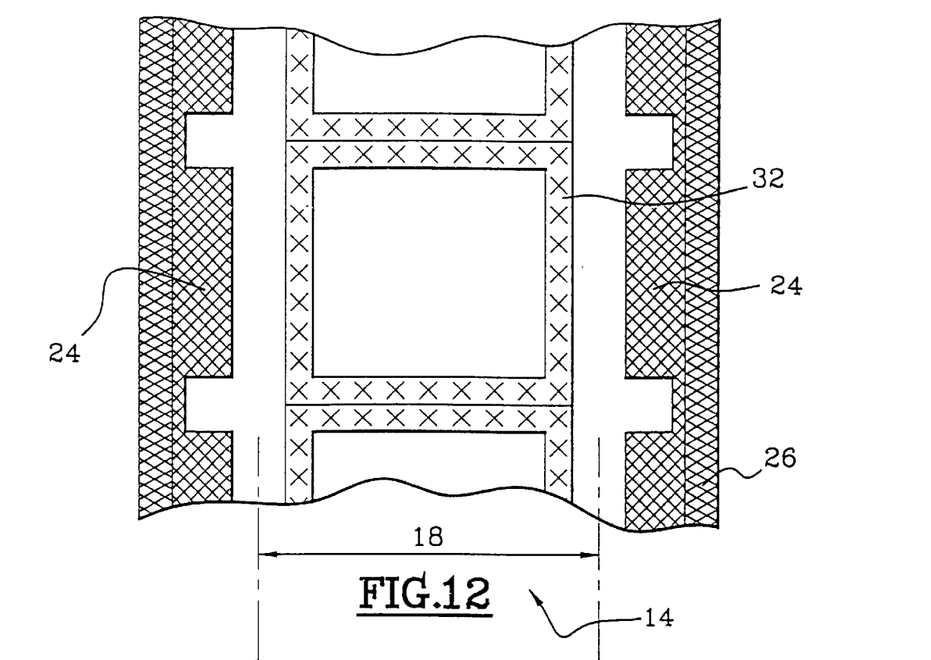
FIGS. 12 and 13 schematically show illustrative active surfaces of a clamping band, two load compensating bands, and two rolling zones fitted on an apparatus cylinder used in marking the edges of formatted products.
Figure 13:
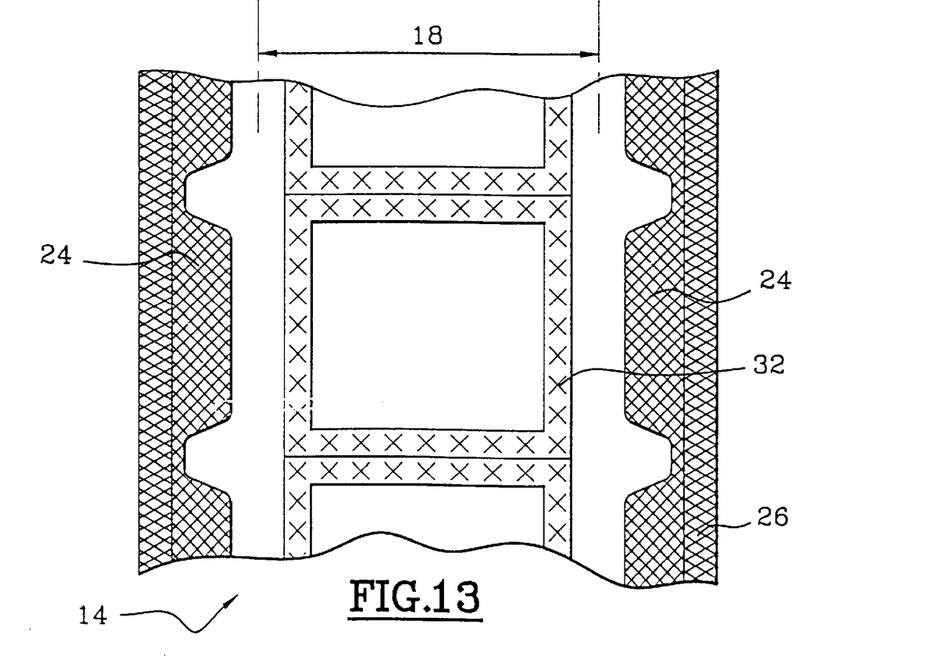

FIGS. 12 and 13 show particular embodiments of the apparatus of the invention for marking the edges of formatted absorbent paper products. Illustratively, such products are table napkins or tissues.

The clamping band 18 of the cylinder 14 is fitted with edge zones 32 having salient elements that mark absorbent paper products composed of at least two plies and to mutually bond these two plies at the edges or peripheral zones of the formatted products.

In such an embodiment, the load compensating band 24 is configured on either side of the clamping band. FIGS. 12 and 13 illustrate two geometric shapes applicable to the load compensating band 24.

The load compensating band 24 also includes a rolling zone 26.

It was shown that with respect to the above embodiment, the load compensating band 24 is situated outside the clamping band 18 of the cylinder 14, the paper sheet 12 moving past the band 18, and that as a result the load compensating band 24 will not leave traces on the paper.

In some applications, however, the paper sheet 12 is used in the manufacture of paper articles of such dimensions that this paper sheet includes trim zones on either side of a useful area. Where appropriate, the load compensating band(s) 24 then can be situated at least partly in the trim zones.

Lastly, in case the load compensating band's salient elements differ from the clamping band's first salient elements, the salient elements of the load compensating band 24 can be sufficiently aesthetic to be kept in the final product, i.e. the paper article. In such a case, the load compensating band 24 can be advantageously configured on the cylinder 14 in such a way that it is at least partly in contact with the paper sheet 12, as a result of which the track of the load compensating band 24 is reproduced at least in part on the paper sheet 12, thus subtending additional marking. The load compensating band's salient elements can be similar to but not identical with (for example being of different sizes) the clamping band, which shall be adapted.

Depending on the configuration of the salient elements of the clamping band 18, it may be the case that the width of the load compensation band 24 required to balance the interacting stresses of the cylinders 14, 16 will exceed the available space on the cylinder 14. If so, one or more partial compensating bands can be used which do not fully compensate the variations in the consecutive instantaneous active surfaces of the clamping band during the rotation of the cylinders 14 and 16, but which nevertheless allow substantially limiting them in order to attain the objective of longer cylinder service life. In this case, the variation among the consecutive instantaneous active surfaces of the clamping band and to the load compensating band is less than the variation in the consecutive instantaneous active surfaces of the single clamping band 18.

Figure 14:
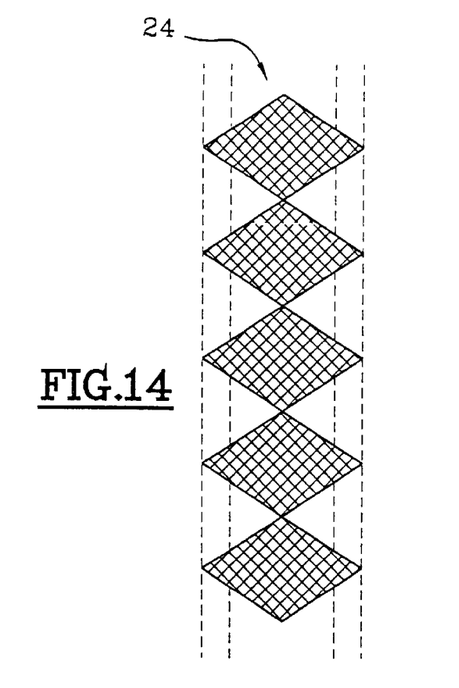
FIG. 14 shows a theoretical load compensating band.
Figure 15:
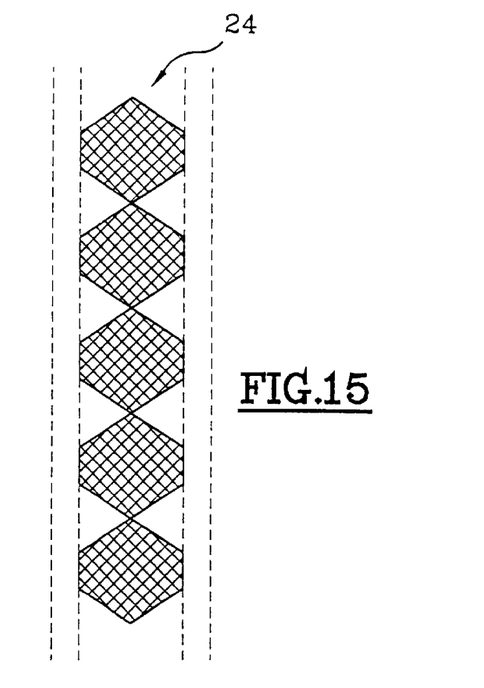
FIGS. 15–17 show illustrative load compensating bands which may be used to take the place of the theoretical load compensating band of FIG. 14.
Figure 16:
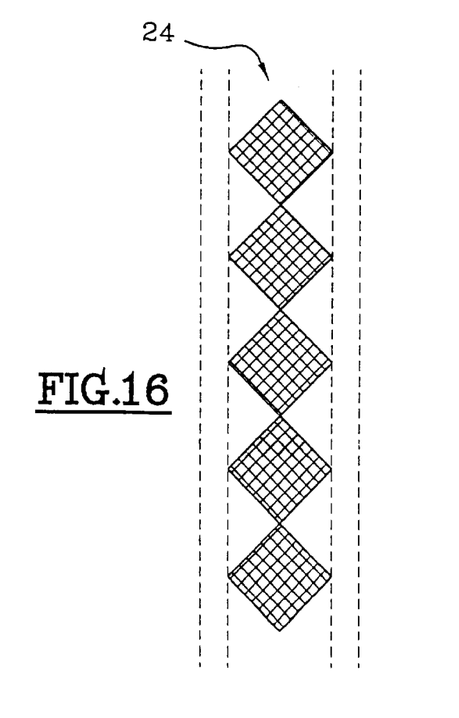
Figure 17:
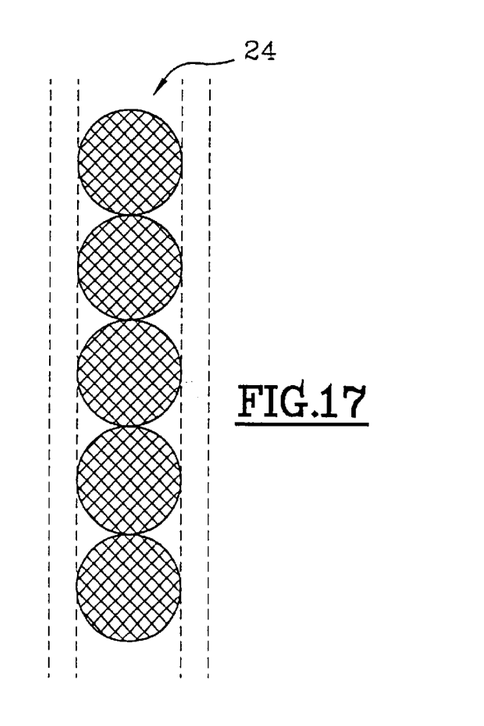

FIGS. 15, 16 and 17 illustrate various designs of a partial compensation band which may replace the theoretical compensation band of FIG. 14 and which includes two edges subtended by a broken line.

In the embodiment of FIG. 15, the theoretical load compensating band has been clipped, that is all portions of the theoretical band of a width exceeding an available maximum width are reduced to the maximum width.

In the embodiment of FIG. 16, the width of the theoretical load compensating band is reduced by a constant factor in order that the maximum width of the partial compensation band does not exceed the maximum available width. In this embodiment, the load compensation band is reduced while the shape of the theoretical compensation band is substantially retained.

Lastly, FIG. 17 shows a third embodiment of a partial compensation band of which the shape is not directly derived from the theoretical band but which nevertheless allows decreasing the stresses between the two cylinders 14, 16. In this embodiment, preference can be given to one of the load compensating band's parameters, for example those zones where the active surface of the compensation is zero, or those zones where it is a maximum, or the transition zones, etc. Using mathematics, the shape of the load compensating band can be derived from the theoretical shape.

The two cylinders of the apparatus of the invention can be made of the same or of a different material. At least one of them is engraved. Both can be made of an undeforming material, such as steel, or one of an undeforming material and the other of a deforming material, such as rubber.

Each cylinder can be composed of a single or of several materials.

In the latter case, the engraved cylinder has a central portion on which to engrave the clamping band's salient elements and which illustratively is made of steel, further of one or more side parts that, when appropriate, are made of another material for the load compensating band, and, as called for, one or more parts situated sideways off the load compensating bands for the rolling zone. These other parts can be made of the same material as the load compensating bands or from another one. The materials used for the load compensating band and for the other parts are undeforming, identical or different. The mating cylinder includes a central portion made, for example of rubber to face the clamping band's salient elements of the engraved cylinder, and it can include one or more lateral parts to face the load compensating band, and, as called for, it can have a rolling zone. These side parts making contact with the load compensating band and possibly with the rolling zone can be made of rubber or from one or more other materials. The side parts respectively correspond to the load compensating band and to the rolling zone which can be made of the same or of a different material.

If the engraved cylinder and its mating cylinder are made of the same material, they can further have different surface treatment zones.

The methods used to operate the apparatus of the invention can lead independently to deforming a paper sheet or to combining several plies of paper or also to simultaneously deform and combine several plies, depending on the methods or the equipment comprising the apparatus of the invention.

In case at least two non-woven or paper plies are combined, the method is applied to apparatus of the invention wherein the plies are clamped between the two cylinders at the clamping band, with or without adhesive being supplied.

In the case of marking in the rigorous sense, a single apparatus of two cylinders, one of which is fitted with a clamping band, can suffice.

Several solutions are feasible for embossing. Illustratively, two plies can be embossed by operating two independent or interacting apparatus and then can be combined by using a third apparatus. Preferably, this third apparatus shares one cylinder (the engraved cylinder) with one of the two other cylinders operating in the embossing mode.

In another embodiments, and still relating to embossing, the first two apparatus are interacting (sharing one cylinder) and each embosses one ply. Ply combination is carried out by apparatus of two cylinders each belonging to the first and second apparatus respectively.

The invention also relates to a method for applying an additive, such as an adhesive, a lotion or ink, to a non-woven or paper sheet where apparatus of the invention is used.

Therefore, the invention makes it possible to manufacture non-woven or paper articles which are marked or embossed in very diverse patterns. The invention also delivers products made up of several plies which are attached to or combined with each other.

It is claimed:

1. Apparatus for clamping at least one paper or non-woven sheet comprising two substantially mutually tangent cylinders with at least one cylinder comprising on an external surface and in a zone which contacts said sheet a clamping band comprising first salient elements, and said cylinders interact in presence or absence of a sheet to subtend an active surface during rotation of the cylinders, wherein at least one of the cylinders comprises an external surface which in a nip makes contact with the other cylinder, by intermediary or not of the sheet by a load-compensating band comprising second salient elements, said nip being selected so that variation of consecutive instantaneous active surfaces of the clamping band and to the load compensating band is less than variation of consecutive instantaneous active surfaces of the clamping band alone.

2. Apparatus as claimed in claim 1, wherein the variation of the consecutive instantaneous active bands of the clamping band and of the load compensating band is substantially zero.

3. Apparatus as claimed in claim 1, wherein the active surface of the load compensating band has a width which alone varies as a function of the instantaneous active surface of the clamping band alone along the circumference of the cylinder on which said load compensating band is present.

4. Apparatus as claimed in claim 1, wherein said cylinders rotate in mutually opposite directions.

5. Apparatus as claimed in claim 1, wherein the first salient elements of the clamping band are identical with or different from the second salient elements of the load compensating band.

6. Apparatus as claimed in claim 1, wherein the load compensating band is configured on a cylinder outside said clamping band.

7. Apparatus as claimed in claim 1, wherein the second salient elements of the load compensating band differ from the first salient elements of the clamping band and the load compensating band at least in part overlaps the clamping band.

8. Apparatus as claimed in claim 1, wherein at least one of the cylinders has at least one clamping band and at least one load compensating band.

9. Apparatus as claimed in claim 8, wherein the second salient elements of the load compensating band are substantially of same height as the first salient elements of the clamping band.

10. Apparatus as claimed in claim 8, wherein the second salient elements of the load compensating band are greater in height than the first salient elements of the clamping band.

11. Apparatus as claimed in claim 8, wherein the second salient elements of the load compensating band are shorter in height than the first salient elements of the clamping band.

12. Apparatus as claimed in claim 1, wherein the load compensating band further comprises a rolling zone which determines a minimum width of the active surface of the load compensating band.

13. Apparatus as claimed in claim 12, wherein the rolling zone of the load compensating band is radially configured at a level at which a remainder of the load compensating band is configured.

14. Apparatus as claimed in claim 12, wherein the rolling band of the load compensating band is radially configured externally to a remainder of the load compensating band.

15. Apparatus as claimed in claim 12, wherein the rolling zone of the load compensating band is radially configured inward relative to a remainder of the load compensating band.

16. Apparatus as claimed in claim 1, wherein more than one load compensating band is present on a common cylinder of said cylinders.

17. Apparatus as claimed in claim 16, wherein each of said more than one load compensating band comprises one rolling zone.

18. Apparatus as claimed in claim 1, wherein the two cylinders are made of undeforming materials.

19. Apparatus as claimed in claim 1, wherein one of the two cylinders is undeforming and another of the two cylinders is deforming.

20. A cylinder to clamp a paper or non-woven sheet comprising a load compensating band as claimed in any one of the above claim 1, 2 or 3.

21. Equipment comprising at least one apparatus as claimed in claim 1, 2 or 3.

22. Equipment comprising at least two of said apparatus as claimed in claim 1, 2 or 3, wherein each of said two apparatus is independent of the other.

23. Equipment comprising at least two of said apparatus as claimed in claim 1, 2 or 3, wherein at least two of said apparatus share one cylinder.

24. A method for combining at least two paper or non-woven plies, comprising operating an apparatus as claimed in claim 1, 2 or 3, and clamping said plies between said two cylinders in an area of the clamping band.

25. A method for marking at least one paper or non-woven sheet comprising operating an apparatus as claimed in claim 1, 2 or 3, and clamping the paper or non-woven sheet between the two cylinders to thereby deform the sheet and provide a pattern on the sheet by means of the clamping band.

26. Method as claimed in claim 25, wherein said clamping of the sheet embosses the sheet.

27. Method as claimed in claim 26, wherein two plies of paper or non-woven sheet are embossed by two of said apparatus and then are joined by another of said apparatus.

28. Method as claimed in claim 27, wherein the apparatus joining the two plies comprises at least one engraved cylinder which is shared with one of the two said apparatus used to emboss the plies.

29. A method of utilizing an apparatus as claimed in claim 1, 2 or 3 including applying an additive to the paper or non-woven sheet.

30. A method for manufacturing tissue paper articles of at least two plies comprising affixing the at least two plies to one another by combining as claimed in claim 24.

31. A method for manufacturing tissue paper articles of at least two plies comprising affixing the at least two plies to one another by marking as claimed in claim 25.

32. A paper or non-woven article comprising at least one ply, wherein said at least one ply is marked by means of the method of claim 25.

* * * * *